US007717915B2

(12) United States Patent
Miyazawa (10) Patent No.: US 7,717,915 B2
(45) Date of Patent: May 18, 2010

(54) ULTRASONIC COAGULATION AND CUTTING APPARATUS

(75) Inventor: Taro Miyazawa, Hino (JP)

(73) Assignee: Olympus Medical Systems Corporation, Tokyo (JP)

( * ) Notice: Subject to any disclaimer, the term of this patent is extended or adjusted under 35 U.S.C. 154(b) by 845 days.

(21) Appl. No.: 11/503,028

(22) Filed: Aug. 11, 2006

(65) Prior Publication Data

US 2007/0043297 A1 Feb. 22, 2007

(30) Foreign Application Priority Data

Aug. 19, 2005 (JP) .............................. 2005-238979

(51) Int. Cl.
*A61B 18/14* (2006.01)
*A61B 17/32* (2006.01)

(52) U.S. Cl. ............................ 606/51; 606/169; 606/45

(58) Field of Classification Search ............. 606/48–52, 606/169
See application file for complete search history.

(56) References Cited

U.S. PATENT DOCUMENTS

| 5,322,055 | A | * | 6/1994 | Davison et al. ................. 601/2 |
| H1745 | H | * | 8/1998 | Paraschac ..................... 606/51 |
| 6,056,735 | A | * | 5/2000 | Okada et al. ................... 606/1 |
| 6,129,735 | A | * | 10/2000 | Okada et al. ................. 606/169 |
| 6,165,191 | A | * | 12/2000 | Shibata et al. ............... 606/169 |
| 6,340,352 | B1 | | 1/2002 | Okada et al. |
| 6,669,690 | B1 | * | 12/2003 | Okada et al. ................... 606/40 |
| 2002/0183774 | A1 | * | 12/2002 | Witt et al. ..................... 606/169 |
| 2004/0102801 | A1 | * | 5/2004 | Cimino ........................ 606/169 |
| 2005/0004589 | A1 | * | 1/2005 | Okada et al. ................. 606/169 |
| 2006/0259054 | A1 | * | 11/2006 | Masuda et al. .............. 606/169 |

FOREIGN PATENT DOCUMENTS

| JP | 08-299351 | 11/1996 |
| JP | 2004-216180 | 8/2004 |
| JP | 2004-283362 | 10/2004 |
| JP | 2004-313342 | 11/2004 |
| WO | WO 2005122918 A1 * | 12/2005 |

* cited by examiner

*Primary Examiner*—Lee S Cohen
*Assistant Examiner*—Benjamin Lee
(74) *Attorney, Agent, or Firm*—Scully, Scott, Murphy & Presser, P.C.

(57) ABSTRACT

An ultrasonic coagulation and cutting apparatus includes: an ultrasonic transducer for a treatment using ultrasonic vibrations on body tissue; a probe for transmitting generated ultrasonic vibrations to the distal end thereof; a movable gripping member for cooperating with the outer surface of the probe in gripping therebetween body tissue; an operation unit operated to move the gripping member; an operation transmitting member for transmitting the operation of the operation unit to the gripping member; and high frequency power supply connecting portions for electrically connecting the probe and the gripping member to predetermined portions of a high frequency power supply for a treatment using high frequency current on the body tissue. At least coagulation of the body tissue using high frequency current is started in a first gripping state. Cutting of the body tissue using ultrasonic vibrations generated by the ultrasonic transducer is started in a second gripping state.

7 Claims, 10 Drawing Sheets

ULTRASONIC COAGULATION AND CUTTING APPARATUS

CROSS REFERENCES TO RELATED APPLICATIONS

This application claims benefit of Japanese Patent Application No. 2005-238979 filed in Japan on Aug. 19, 2005, the contents of which are incorporated by this reference.

BACKGROUND OF THE INVENTION

1. Field of the Invention

The present invention relates to an ultrasonic coagulation and cutting apparatus for gripping body tissue and performing coagulation using high frequency current and/or cutting using ultrasonic vibrations of the body tissue.

2. Description of the Related Art

In recent years, observations of body cavities and organs have been performed using endoscopes, an insertion portion of each endoscope being inserted into a body cavity. In addition, various treatments and therapies have also been performed under endoscopic observation. In cutting or coagulation of body tissue under endoscopic observation, an ultrasonic instrument for treatment or a diathermy instrument for treatment is used. The ultrasonic instrument transmits ultrasonic vibrations to body tissue to perform a treatment using frictional heat. The diathermy instrument supplies high frequency current to body tissue to perform a treatment using Joule heat.

Using ultrasonic vibrations, the ultrasonic instrument permits a tool for treatment to generate frictional heat, thus cutting body tissue while coagulating the tissue. The ultrasonic instrument performs coagulation and cutting as one action using frictional heat. Unfortunately, the ultrasonic instrument has a tendency that cutting power is reduced when coagulating power is increased. In particular, tissue cutting involving blood vessel clotting needs high coagulating power. However, reducing cutting power drastically leads to stress on a user. It is, therefore, difficult to realize high levels of both coagulation and cutting.

The diathermy instrument using high frequency current allows an energized electrode to come into contact with body tissue, thus performing cutting or coagulation of the tissue. Diathermy instruments are broadly classified into monopolar and bipolar types. The monopolar type instrument has the following structure: One of two dedicated terminals provided for a power supply unit for generating high frequency current is connected to an active electrode to be in contact with a target area of body tissue. The other terminal is connected to a feedback electrode to be in face contact with a wide range of a body surface except the target area.

The bipolar type instrument has the following structure: Two dedicated terminals provided for a power supply unit for generating high frequency current are connected to two active electrodes arranged in the instrument main body. Accordingly, the bipolar type needs no feedback electrode and is suitable for a treatment, such as blood vessel clotting, because a continuity path for the flow of current can be specified.

For example, when a treatment for blood vessel clotting is performed with the ultrasonic instrument, cutting is performed while coagulation is being performed. In the ultrasonic instrument, therefore, it is difficult to simultaneously realize high coagulating power and high cutting speed.

On the other hand, in the case where a treatment for blood vessel clotting is performed with the bipolar type diathermy instrument, although the bipolar type has high coagulating power, cutting is fundamentally performed using another instrument instead of the bipolar type diathermy instrument. In other words, a user has to often change the instrument. Disadvantageously, the operation is complicated.

Japanese Unexamined Patent Application Publication No. 2004-216180 discloses an ultrasonic cutting and coagulation apparatus capable of easily performing a treatment using ultrasonic vibrations and a treatment using high frequency current on body tissue in an appropriate manner. In this apparatus, a movable handle is operated to be closed such that a gripping member is brought into contact with a probe to grip body tissue. In this gripping state, when the treatment using ultrasonic vibrations is performed, a power supply for driving an ultrasonic transducer supplies driving current to the ultrasonic transducer. Consequently, the ultrasonic transducer is driven, thus transmitting ultrasonic vibrations generated by the ultrasonic transducer to the probe. Thus, the gripped body tissue is coagulated and cut.

On the other hand, when the treatment using high frequency current is performed in the gripping state, high frequency current is supplied from a high frequency power supply to either the gripping member or the probe, alternatively, to both of them. Consequently, the high frequency current flows from the gripping member or the probe to a counter electrode plate via the body tissue and is fed back to the high frequency power supply. Thus, the gripped tissue is cut or coagulated.

SUMMARY OF THE INVENTION

According to the present invention, there is provided an ultrasonic coagulation and cutting apparatus including: an ultrasonic transducer for converting electric signals into ultrasonic vibrations to perform a treatment using ultrasonic vibrations on body tissue; a probe including a rod member having a predetermined length and a predetermined outer diameter, the probe transmitting ultrasonic vibrations generated by the ultrasonic transducer to the distal end thereof, the proximal end thereof being connected to the ultrasonic transducer; a gripping member for cooperating with the outer surface of the probe in gripping therebetween body tissue, the member being movable closer to and farther away from the probe so that the gripped body tissue is coagulated and cut; an operation unit operated to move the gripping member closer to or farther away from the probe; an operation transmitting member for transmitting the operation of the operation unit to the gripping member such that the gripping member is moved closer to or farther away from the probe in accordance with the amount of operating the operation unit; and high frequency power supply connecting portions for electrically connecting the probe and the gripping member to predetermined portions of a high frequency power supply to perform a treatment using high frequency current on the body tissue.

In the ultrasonic coagulation and cutting apparatus, coagulation of body tissue using high frequency current supplied from the high frequency power supply is started in a first gripping state in which the body tissue is gripped between the outer surface of the probe and the gripping member moved closer thereto by operating the operation unit. Cutting of the body tissue, including coagulated part, using ultrasonic vibrations generated by the ultrasonic transducer is started in a second gripping state in which the gripping member is further moved closer to the probe after the coagulation of the body tissue is performed.

The above and other objects, features and advantages of the invention will become more clearly understood from the following description referring to the accompanying drawings.

DESCRIPTION OF THE PREFERRED EMBODIMENTS

Embodiments of the present invention will now be described below with reference to the drawings.

An embodiment of the present invention will now be described with reference to FIGS. 1 to 9.

Figure 1:
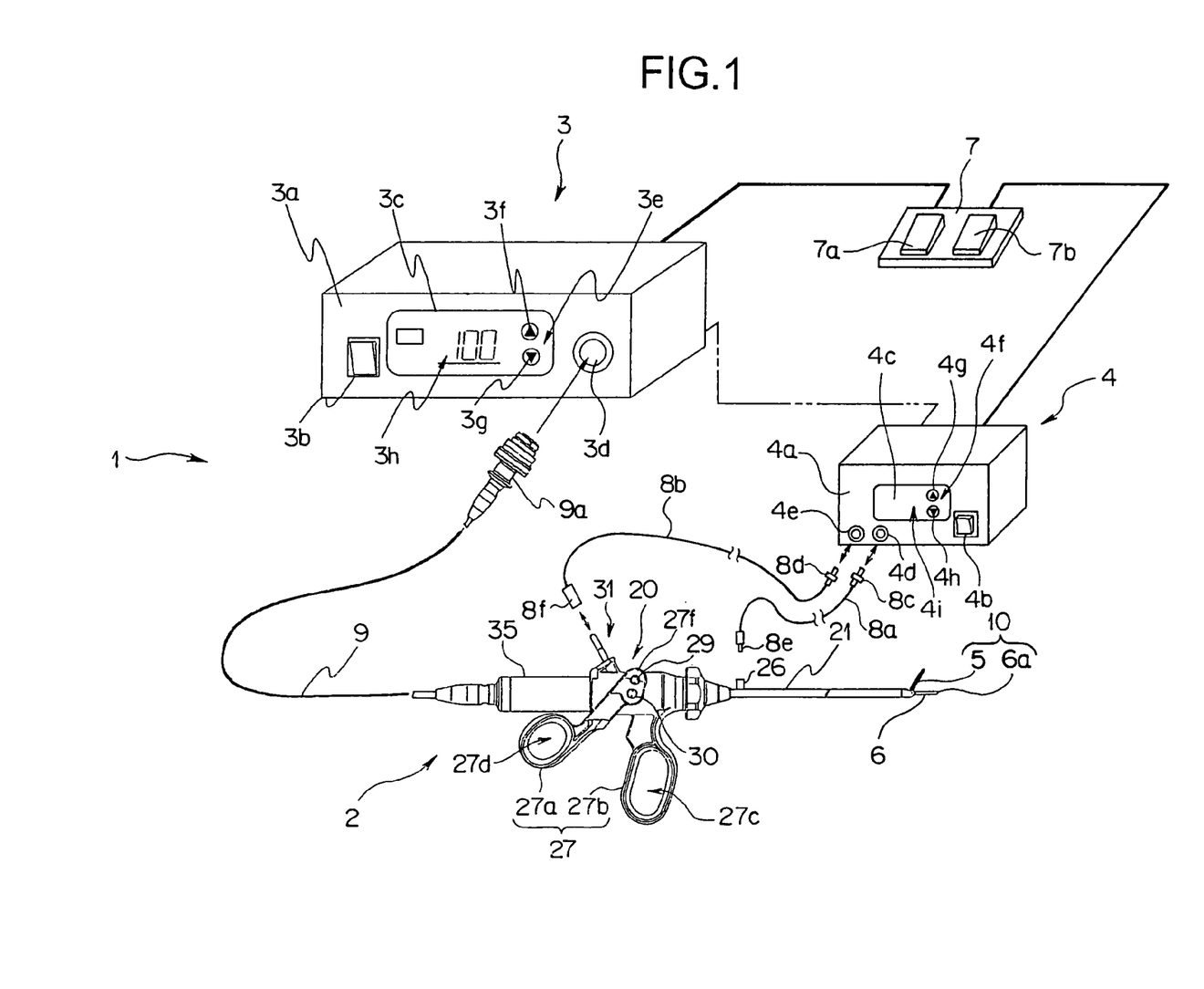
FIG. 1 is a diagram explaining the configuration of an ultrasonic coagulation and cutting apparatus according to an embodiment of the present invention.

Referring to FIG. 1, according to the present embodiment, an ultrasonic coagulation and cutting apparatus 1 includes an ultrasonic coagulation and cutting instrument (hereinafter, referred to as an ultrasonic instrument) 2, an ultrasonic surgical unit 3, and a diathermy surgical unit 4.

The ultrasonic instrument 2 includes a control portion 20 and an elongated sheath 21 extending from the distal end of the control portion 20. The control portion 20 has a casing 35 of a transducer unit 2b, the casing 35 being arranged at the proximal end of the control portion 20. In the casing 35, an ultrasonic transducer (not shown) for converting electric signals into mechanical vibrations is disposed. The sheath 21 has a treatment tool 10 at the distal end thereof. The treatment tool 10 includes a gripping member 5 that is pivotable as will be described below and a distal end 6a of a probe 6. The probe 6 transmits the ultrasonic vibrations generated by the ultrasonic transducer toward its distal end, constituting the treatment tool 10. According to the present embodiment, the ultrasonic coagulation and cutting apparatus 1 performs a treatment using high frequency current and that using ultrasonic vibrations on body tissue gripped by the treatment tool 10.

The ultrasonic surgical unit 3 has a control panel 3a. The control panel 3a includes a power switch 3b, an operation display panel 3c, and a port 3d for electric cable connection. The operation display panel 3c includes a set switch 3e and an indicator 3h. The set switch 3e is used to specify an ultrasonic output value, i.e., control a cutting power level. The set switch 3e includes an UP switch 3f and a DOWN switch 3g. With these arrangements, a cutting power level can be properly changed. The indicator 3h indicates, e.g., an ultrasonic output value set using the set switch 3e in a digital form on a display area. The ultrasonic surgical unit 3 includes a drive circuit (not shown) therein. The drive circuit supplies electric energy to the ultrasonic transducer disposed in the ultrasonic instrument 2, thus generating ultrasonic vibrations.

The diathermy surgical unit 4 includes a control panel 4a. The control panel 4a includes a power switch 4b, an operation display panel 4c, and a pair of ports 4d and 4e for electric cable connection. The operation display panel 4c includes a set switch 4f and an indicator 4i. The set switch 4f is used to specify a high frequency output value, i.e., control a coagulating power level. The set switch 4f includes an UP switch 4g and a DOWN switch 4h. With these arrangements, a coagulating power level can be properly changed. The indicator 4i indicates, e.g., a high frequency output value set using the set switch 4f in a digital form on a display area. The diathermy surgical unit 4 includes a high frequency generating circuit (not shown) therein. The high frequency generating circuit generates high frequency current based on a set value set using the set switch 4f.

A foot switch 7 is detachably connected to the ultrasonic surgical unit 3 and the diathermy surgical unit 4. The foot switch 7 includes, e.g., a switch 7a for coagulation and a switch 7b for coagulation and cutting. When the switch 7a is turned on, the diathermy surgical unit 4 supplies high frequency current to the ultrasonic instrument 2. When the switch 7b is turned on, the ultrasonic surgical unit 3 supplies electric energy for ultrasonic vibrations to the ultrasonic instrument 2 and the diathermy surgical unit 4 also supplies high frequency current to the ultrasonic instrument 2.

The ultrasonic coagulation and cutting apparatus 1 includes a first electric cable 8a for high frequency current, a second electric cable 8b for high frequency current, and an electric cable 9 for ultrasonic waves. A connector 8c arranged at one end of the first electric cable 8a is detachably connected to the port 4d. A connector 8d arranged at one end of the second electric cable 8b is detachably connected to the port 4e. A connector 9a arranged at one end of the electric cable 9 is detachably connected to the port 3d.

Figure 2:
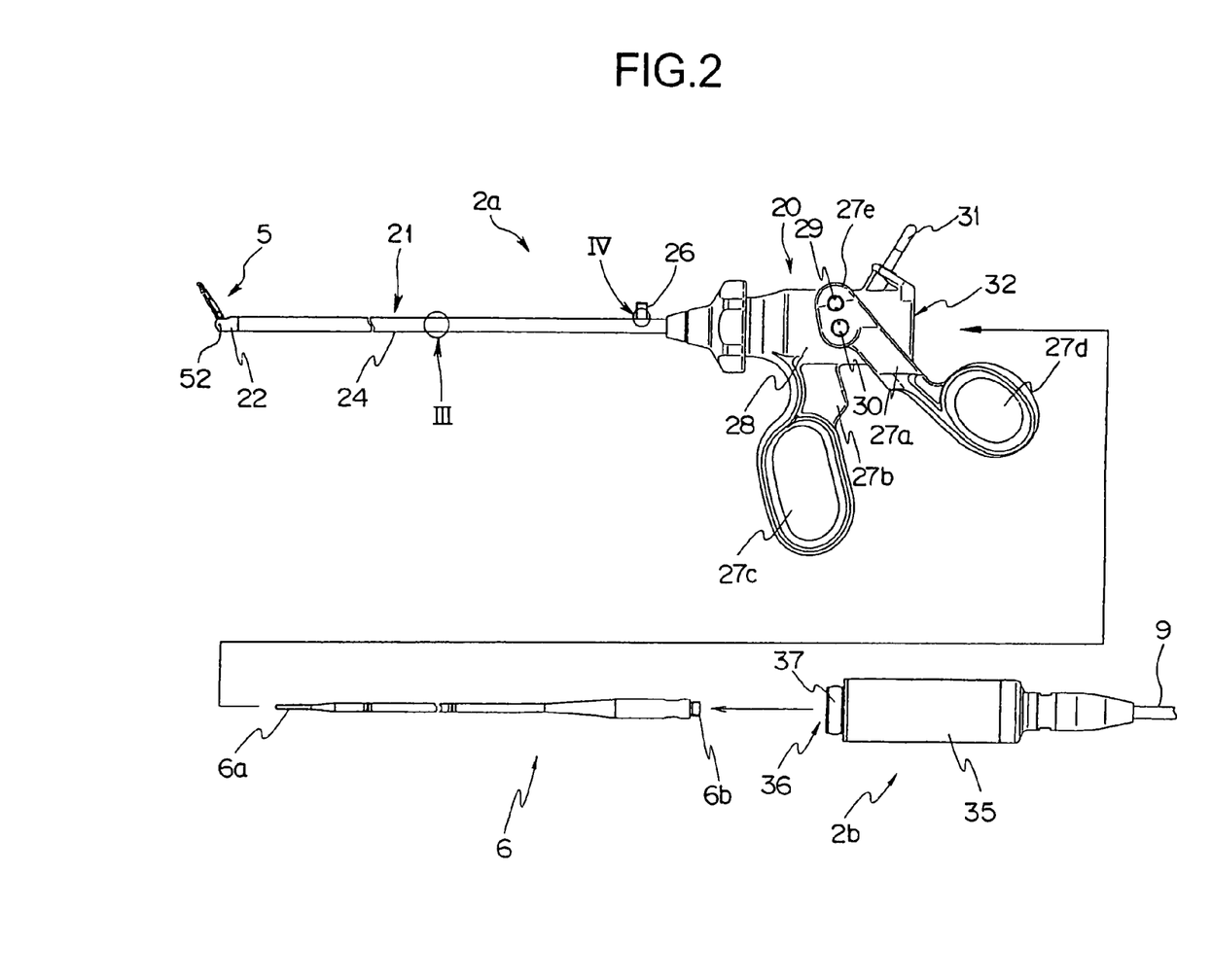
FIG. 2 is a side plan view of the ultrasonic coagulation and cutting apparatus which is divided into three parts.

Referring to FIG. 2, the ultrasonic instrument 2 includes a handle unit 2a, the probe 6, and the transducer unit 2b. The components are detachable from each other. In other words, the ultrasonic instrument 2 can be divided into three parts.

The transducer unit 2b includes the casing 35 which is detachably connected to the control portion 20 of the handle unit 2a. The casing 35 includes therein the ultrasonic transducer for generating ultrasonic vibrations. The casing 35 has a unit coupler 36 at the distal end thereof. The unit coupler 36 includes a catching ring 37 on its periphery. The catching ring 37 is a C-shaped ring obtained by removing a part of a ring member. The casing 35 is constructed such that the electric cable 9 is detachably connected to the proximal end thereof.

The probe 6 is a rod member made of, e.g., titanium alloy having the excellent acoustic property of transmitting ultrasonic vibrations and exhibiting good conductivity in a region from the proximal end to the distal end thereof. The probe 6 is formed in a predetermined shape, i.e., the length and outer diameter of the probe 6 are previously set so that the probe 6 resonates at the most suitable frequency for ultrasonic treatment. The distal end 6a of the probe 6 is a part to be in contact with body tissue. The probe 6 has a mounting screw 6b at the proximal end thereof. The mounting screw 6b is to be fastened into a screw hole (not shown) formed in the ultrasonic transducer. The mounting screw 6b of the probe 6 is fastened into the screw hole of the ultrasonic transducer, so that ultrasonic vibrations generated by the ultrasonic transducer are transmitted to the distal end 6a.

The handle unit 2a includes the control portion 20, the sheath 21, and the gripping member 5. The sheath 21 is integrated with a support 22 arranged in the distal end thereof and a pipe 23 arranged in the proximal end thereof.

Figure 3:
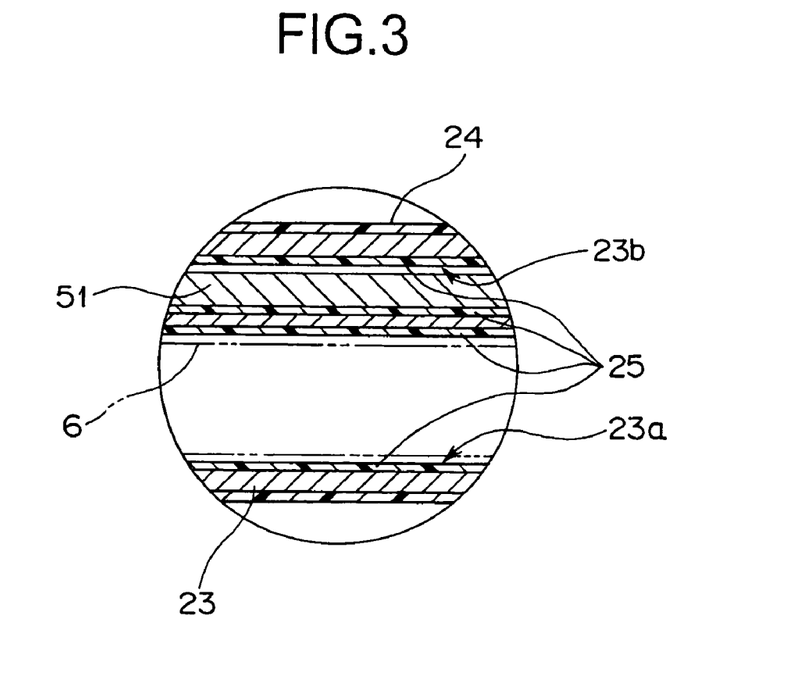
FIG. 3 is an enlarged sectional view of part shown by an arrow III in FIG. 2.

The pipe 23 is made of a conductive material. The pipe 23 includes a main channel 23a and a sub-channel 23b which are respectively formed in predetermined shapes. Referring to FIG. 3, the main channel 23a is a hole through which the probe 6 is inserted as shown by alternate long and two short dashes lines. The sub-channel 23b is a hole through which a control rod 51 is slidably arranged. The control rod 51 is an operation transmitting member for rotating the gripping member 5.

Each of the main channel 23a and the sub-channel 23b has an insulating film 25 made of, e.g., an epoxy resin nanocomposite, on the inner surface.

Figure 4:
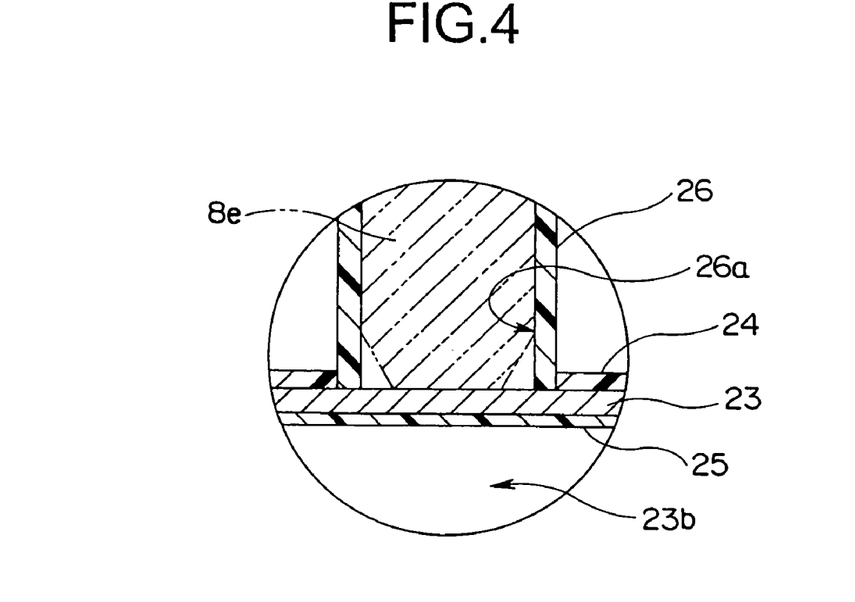
FIG. 4 is an enlarge sectional view of part shown by an arrow IV in FIG. 2.

Referring to FIG. 4, the pipe 23 has a tubular body 24 on the outer surface. The tubular body 24 is made of an insulating material, e.g., polytetrafluoroethylene.

The pipe 23 includes a first-electric-cable connecting portion 26, serving as a high frequency power supply connecting portion, at the proximal end thereof. The first-electric-cable connecting portion 26 is a tubular insulating member. The first-electric-cable connecting portion 26 has a female thread 26a on the inner surface. A connecting screw 8e arranged at the other end of the first electric cable 8a is screwed into the female thread 26a. Screwing the connecting screw 8e into the female thread 26a allows the end face of the connecting screw 8e to come into contact with the outer surface of the pipe 23. In other words, a predetermined engagement between the connecting screw 8e and the female thread 26a in the first-electric-cable connecting portion 26 permits electrical continuity between the first electric cable 8a and the pipe 23.

Figure 5:
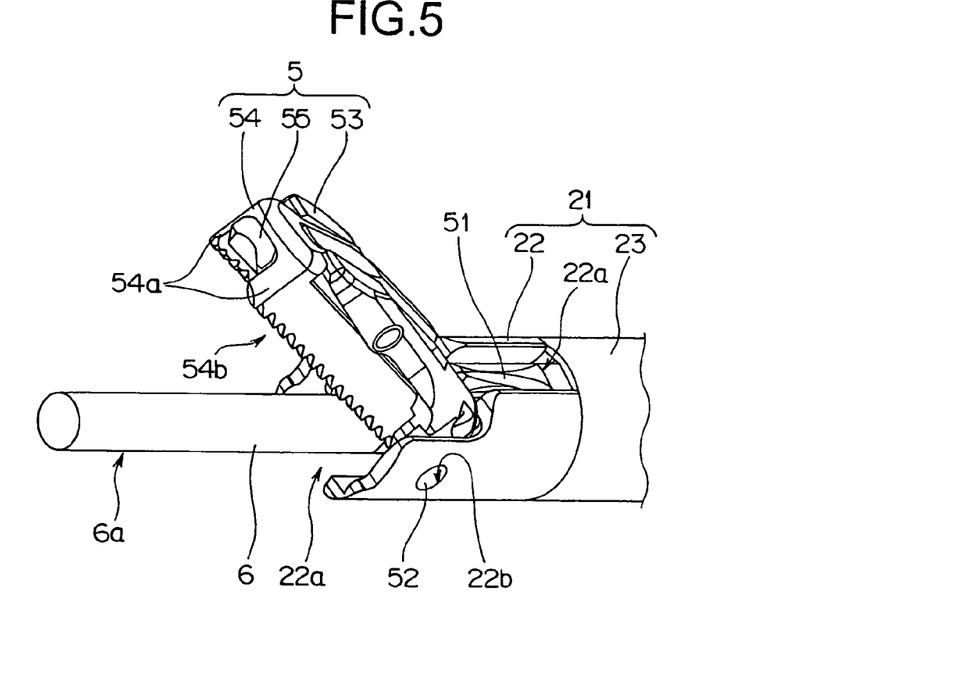
FIG. 5 is a perspective view of a treatment tool.

Referring to FIG. 5, the support 22 is made of a conductive material. The support 22 is coupled with the pipe 23 through, e.g., a coupling member (not shown) having conductivity. Accordingly, the support 22 and the pipe 23 are in electrical continuity with each other. The support 22 has a notch 22a obtained by removing upper and lower parts of the support 22 in FIG. 5. The width of the notch 22a is set such that the gripping member 5 is pivotable about the proximal end thereof. In each side surface of the support 22 having the notch 22a, a shaft hole 22b is formed to receive a shaft 52.

The support 22 has a main channel (not shown) in which the probe 6 is arranged and a sub-channel (not shown) through which the control rod 51 is disposed. Each of the outer surface of the support 22, the inner surface of the main channel, and the inner surface of the sub-channel is covered with an insulating film (not shown).

Figure 6:
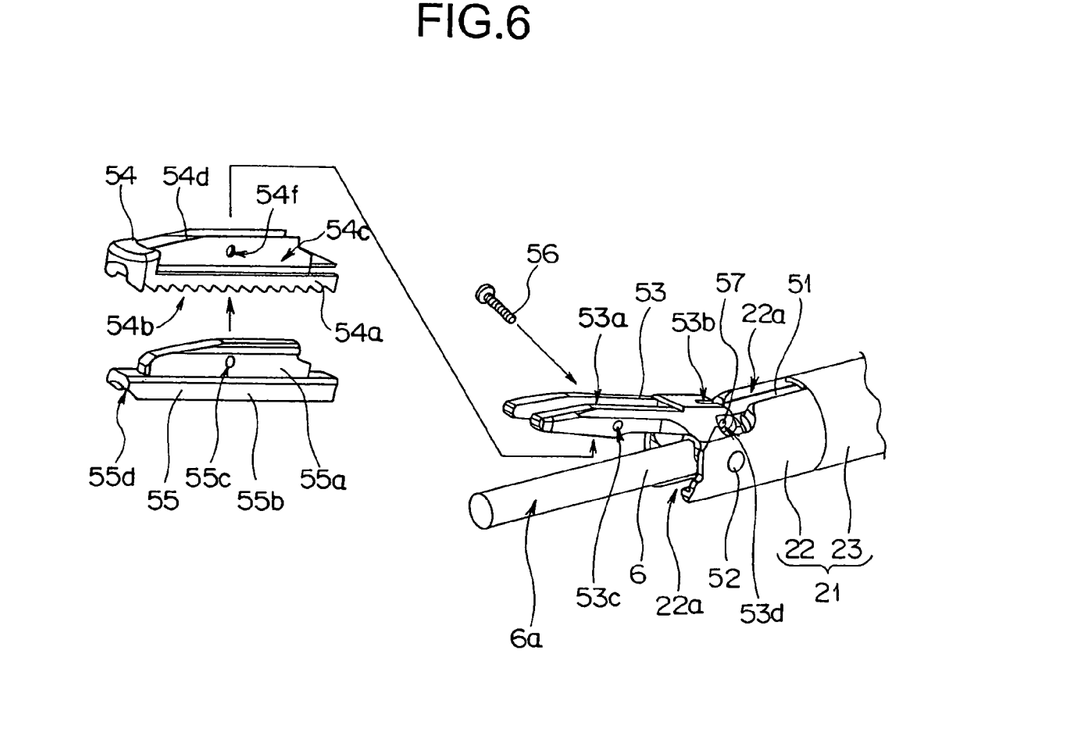
FIG. 6 includes a perspective view of the treatment tool and an exploded perspective view of a gripping member.
Figure 7:
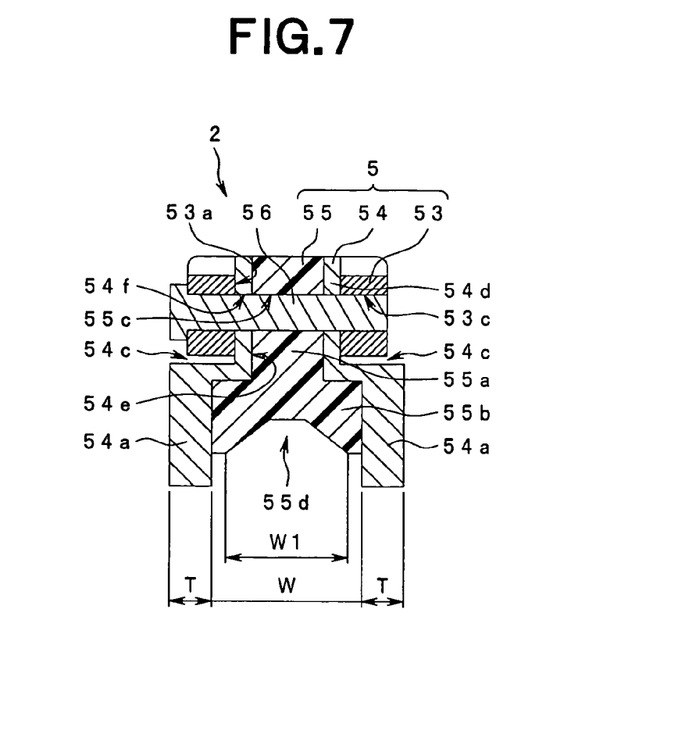
FIG. 7 is a cross-sectional view of the gripping member taken along at an axis of a fixing screw fitted in the gripping member.

As shown in FIGS. 5 to 7, the gripping member 5 is pivotably attached to the support 22 through the shaft 52. The gripping member 5 includes a main body 53, a member 54 for diathermy, a member 55 for ultrasonic treatment.

The main body 53 is made of a conductive material. The main body 53 serves as a substantially H-shaped coupling member having two bifurcated portions. The main body 53 further includes a first notch 53a in which the diathermy member 54 is arranged and a second notch 53b in which the distal end of the control rod 51 is disposed.

In the main body 53, a screw hole 53c, into which a fixing screw 56 is screwed, is formed at a predetermined position in each side wall adjacent to the first notch 53a. Further, a pin hole 53d, into which a pin 57 is fitted, is formed at a predetermined position in each side wall adjacent to the second notch 53b.

In the main body 53, a hole (not shown), through which the shaft 52 is inserted, is formed in the distal end. In other words, the main body 53 constituting the gripping member 5 is coupled with the support 22 so as to pivot substantially about the shaft 52. Accordingly, the support 22 and the main body 53 are in electrical continuity with each other.

The diathermy member 54 is made of a conductive material. The diathermy member 54 includes a bifurcated toothed gripping portion (hereinafter, referred to as a bifurcated toothed portion) 54a, serving as the bottom surface in FIGS. 5 to 7. An interval W between segments of the bifurcated toothed portion 54a is set in consideration of the diameter of the distal end 6a of the probe 6. Specifically, the diathermy member 54 has a recess whose width is larger than the diameter of the distal end 6a by a predetermined amount to keep the bifurcated toothed portion 54a from contact with the distal end 6a while the bifurcated toothed portion 54a is being rotated. The thickness T of each segment of the bifurcated toothed portion 54a is appropriately set in consideration of the rigidity and the coagulation capability. In the diathermy member 54, teeth 54b for securely gripping body tissue are arranged in, e.g., a row on the bottom surfaces of the segments of the bifurcated toothed portion 54a including edges of the recess.

The diathermy member 54 has notches 54c extending in the lengthwise direction thereof in both upper side surfaces. The notches 54c are used to adjust the width of the upper part of the diathermy member 54. Since the diathermy member 54 has the notches 54c, a projection 54d is formed in the upper part of the diathermy member 54. The projection 54d is arranged in the first notch 53a.

The diathermy member 54 has a through-hole 54e in which the ultrasonic treatment member 55 is arranged at a predetermined position. The cross section of the through-hole 54e is, e.g., rectangular. In addition, the diathermy member 54 has holes 54f, through which the fixing screw 56 is inserted. Each hole 54f is formed at a predetermined position in the corresponding side wall of the projection 54d.

The ultrasonic treatment member 55 is made of at least a flexible non-damping material, e.g., polytetrafluoroethylene. The flexible non-damping material is a flexible material having the property that does not inhibit vibrations. When the distal end 6a of the probe 6 is brought into contact with the ultrasonic treatment member 55 comprising the flexible non-damping material, any impact is not given to the distal end 6a and ultrasonic vibrations transmitted from the distal end 6a are not inhibited. The ultrasonic treatment member 55 may be made of a conductive material obtained by mixing conductive particles into the flexible non-damping material.

The ultrasonic treatment member 55 serves as a probe contact member to be in contact with the probe 6 and is constructed in consideration of the contact with the distal end 6a of the probe 6. Central part of the cross-section of the ultrasonic treatment member 55 projects higher than both side parts thereof. The ultrasonic treatment member 55 includes a projection 55a for attachment and a tissue pressing portion 55b. The attachment projection 55a is shaped so as to fit in the through-hole 54e of the diathermy member 54. The ultrasonic treatment member 55 has a hole 55c, through which the fixing screw 56 is inserted, in a predetermined position of the attachment projection 55a. The tissue pressing portion 55b is shaped so as to receive, e.g., a blood vessel in a recess. The tissue pressing portion 55b has a recess 55d in the bottom surface thereof to prevent the distal end 6a of the probe 6 from being moved toward either segment of the bifurcated toothed portion 54a when the tissue pressing portion 55b is in contact with the distal end 6a. The width W1 of an opening of the recess 55d is larger than the diameter of the distal end 6a of the probe 6 by a predetermined amount. Consequently, the distal end 6a is reliably guided into the recess 55d.

The gripping member 5 is pivotably attached to the support 22 in, e.g., the following procedure.

First, the main body 53 constituting the gripping member 5 is pivotably coupled with the support 22. Subsequently, the diathermy member 54 is combined with the ultrasonic treatment member 55. Accordingly, the attachment projection 55a of the ultrasonic treatment member 55 is fitted into the through-hole 54e of the diathermy member 54. In this state, the projection 54d of the diathermy member 54 is received in the first notch 53a of the main body 53. After that, the diathermy member 54 and the ultrasonic treatment member 55 are fastened to the main body 53 by the fixing screw 56.

With these arrangements, the gripping member 5 is pivotably attached to the support 22. In this state, the inner surface of the first notch 53a in the main body 53 is in contact with the side surfaces of the projection 54d constituting the diathermy member 54. Thus, the main body 53 and the diathermy member 54 are brought into electrical continuity with each other. In addition, a combined unit comprising the diathermy member 54 and the ultrasonic treatment member 55 is rotatable about the fixing screw 56 like a seesaw. Accordingly, even if the bifurcated toothed portion 54a is worn, the degree of contact between the diathermy member 54 and body tissue is changed so that the tissue can be securely gripped.

Figure 8:
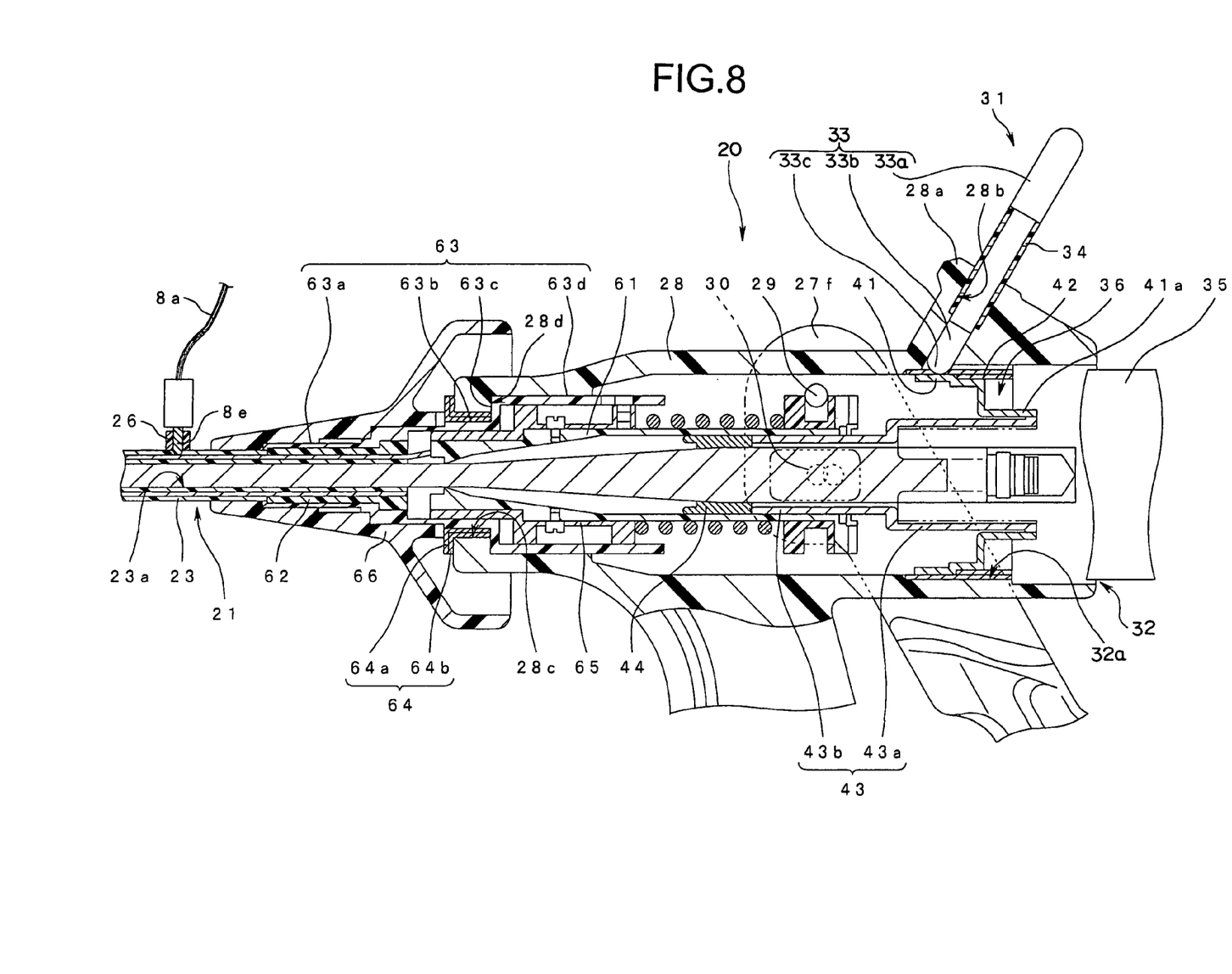
FIG. 8 is a sectional view of a control portion, explaining a continuity path for the flow of current between a probe, constituting an ultrasonic coagulation and cutting instrument, and high frequency power supply connecting portions.

As shown in FIGS. 1, 2, and 8, the control portion 20 of the handle unit 2a is located at the proximal end of the sheath 21. The control portion 20 includes a control handle 27, serving as a closable operation unit for rotating the gripping member 5. The control handle 27 includes a movable handle 27a and a fixed handle 27b. The fixed handle 27b has a finger catch hole 27c in one end to be operated. The movable handle 27a has a finger catch hole 27d in one end to be operated. Generally, fingers except the thumb of one hand are selectively inserted into the finger catch hole 27c and the thumb of the same hand is inserted into the finger catch hole 27d.

The fixed handle 27b and the movable handle 27a constituting the control handle 27 are arranged at predetermined positions in a control-portion main body 28, which constitutes the control portion 20. Upper part of the fixed handle 27b is integrated with the main body 28 in a one-piece design. The upper end of the movable handle 27a is divided into bifurcated coupling portions 27e and 27f, which are arranged on both sides of the main body 28. Each of the coupling portions 27e and 27f includes a handle pivot shaft 29 in the upper part. The handle pivot shafts 29 project inwardly so as to face each other. Those handle pivot shafts 29 are coupled with the main body 28 above an axis of the sheath 21, thus forming a fulcrum. Consequently, the movable handle 27a is pivotable about the handle pivot shafts 29. Each handle pivot shaft 29 is covered with an insulating cap (not shown) for high frequency insulation.

In the movable handle 27a, each of the coupling portions 27e and 27f includes an operating pin 30. Each operating pin 30 is located below the corresponding handle pivot shaft 29 in FIG. 8. Each operating pin 30 is a member for transmitting driving force to the control rod 51 inserted through the sheath 21. The control rod 51 is movable forward and backward in the axial direction in accordance with the pivoting operation of the movable handle 27a. Consequently, the gripping member 5 is pivotable about the shaft 52. The operating pins 30 are arranged substantially on the axis of the sheath 21.

The control portion 20 includes a second-electric-cable connecting portion 31, serving as a high frequency power supply connecting portion. The second-electric-cable connecting portion 31 is electrically connected to a plug 8f provided for the other end of the second electric cable 8b.

The control-portion main body 28 is made of an insulating material and is substantially cylindrical. The main body 28 has an electrode mounting portion 28a. An electrode pin 33 constituting the second-electric-cable connecting portion 31 is arranged in the electrode mounting portion 28a. The electrode pin 33 is inserted into an electrode-pin hole 28b formed in the electrode mounting portion 28a. One end of the electrode pin 33 serves as a connection portion 33a connected to the plug 8f of the second electric cable 8b. The connection portion 33a is shaped in a predetermined form. A fixing screw portion 33b is formed in the other end of the electrode pin 33. In other words, the electrode pin 33 is screwed into the electrode-pin hole 28b. The middle of the electrode pin 33 is covered with an electrode insulating cover 34. The electrode pin 33 has a conical tip 33c located at the end of the screw portion 33b, the tip 33c being in contact with the outer surface of a connection member 41 shown in FIG. 8 which will be described below.

The control-portion main body 28 has a transducer connector 32 at the proximal end thereof. The transducer connector 32 is detachably connected to the unit coupler 36. The transducer connector 32 has a female thread 32a on the inner surface thereof. The connection member 41, made of a conductive material, is stepped ring-shaped. The connection member 41 and a fixing ring 42 are sequentially screwed into the female thread 32a. In other words, the connection member 41 is integrally fixed to a predetermined position at the proximal end of the control-portion main body 28 by the fixing ring 42.

A large-diameter portion 43a constituting a conductive cylinder 43 is received in a small-diameter portion 41a constituting the connection member 41. The conductive cylinder 43 includes the large-diameter portion 43a and a small-diameter portion 43b. The small-diameter portion 43b has a probe holder 44 at the distal end thereof. The probe holder 44 is made of conductive silicone rubber, serving as an elastic conductive material, and is ring-shaped.

To construct the ultrasonic instrument 2 shown in FIG. 1, a worker first screws the mounting screw 6b provided for the probe 6 into the ultrasonic transducer. Thus, the probe 6 is combined with the transducer unit 2b in one unit. In this state, the worker disposes the transducer unit 2b combined with the probe 6 to the handle unit 2a through the transducer connector 32, thus assembling the ultrasonic instrument 2.

At that time, the probe 6 is arranged at a predetermined position in the control-portion main body 28 constituting the control portion 20. Predetermined part of the probe 6 is in tight contact with the inner surface of the probe holder 44. Therefore, the probe 6 is brought into electrical continuity with the electrode pin 33 through the probe holder 44, the conductive cylinder 43, and the connection member 41.

A slider attaching member 61 made of an insulating material is engaged with the outer surface of the small-diameter portion 43b constituting the conductive cylinder 43. The slider attaching member 61 is arranged so as to partially cover the probe 6. The pipe 23 has the main channel 23a through which the probe 6 is inserted. A pipe fixing member 62 comprising an insulating material is fixed to the proximal end of the pipe 23. The pipe fixing member 62 is integrally fixed to a projected end 63a of an eccentric cylinder 63.

The eccentric cylinder 63 is fixed to an inwardly flanged open end 28c at the distal end of the control-portion main body 28 through a fixing ring 64. In other words, the fixing ring 64 having a flange 64a is arranged in the flanged open end 28c. The fixing ring 64 has a female thread 64b on the inner surface thereof. A male thread 63b formed on the eccentric cylinder 63 is engaged with the female thread 64b. In other words, the worker arranges the fixing ring 64 in the flanged open end 28c. While keeping this arrangement, the worker screws the male thread 63b on the eccentric cylinder 63 into the female thread 64b on the fixing ring 64. Consequently, a shoulder 63c of the eccentric cylinder 63 is brought into contact with a flanged face 28d of the control-portion main body 28, thus combining the eccentric cylinder 63 with the main body 28. Consequently, the probe 6 is arranged in the ultrasonic instrument 2 such that the probe 6 is kept insulated.

A rotary cylinder 63d constituting the eccentric cylinder 63 includes a drive-shaft connecting member 65, serving as a member movable forward and backward along an axis thereof. The distal end of the drive-shaft connecting member 65 is fixed to the proximal end of the control rod 51.

A rotatable knob 66 is integrally attached to the proximal end of the sheath 21 such that the knob 66 is rotatable about an axis of the distal end of the control-portion main body 28.

The operation of the ultrasonic coagulation and cutting apparatus 1 with the above-described structure will now be described.

First, a user prepares the first and second electric cables 8a and 8b and the electric cable 9 for ultrasonic waves. The user connects the connector 8c of the first electric cable 8a to the port 4d provided for the diathermy surgical unit 4. The user screws the connecting screw 8e of the first electric cable 8a into the first-electric-cable connecting portion 26 provided for the ultrasonic instrument 2 to provide a predetermined connection state.

The user connects the connector 8d of the second electric cable 8b to the port 4e provided for the diathermy surgical unit 4. In addition, the user connects the plug 8f of the second electric cable 8b to the second-electric-cable connecting portion 31 provided for the ultrasonic instrument 2 in a predetermined state.

The user connects the connector 9a of the electric cable 9 to the port 3d of the ultrasonic surgical unit 3.

Figure 9:
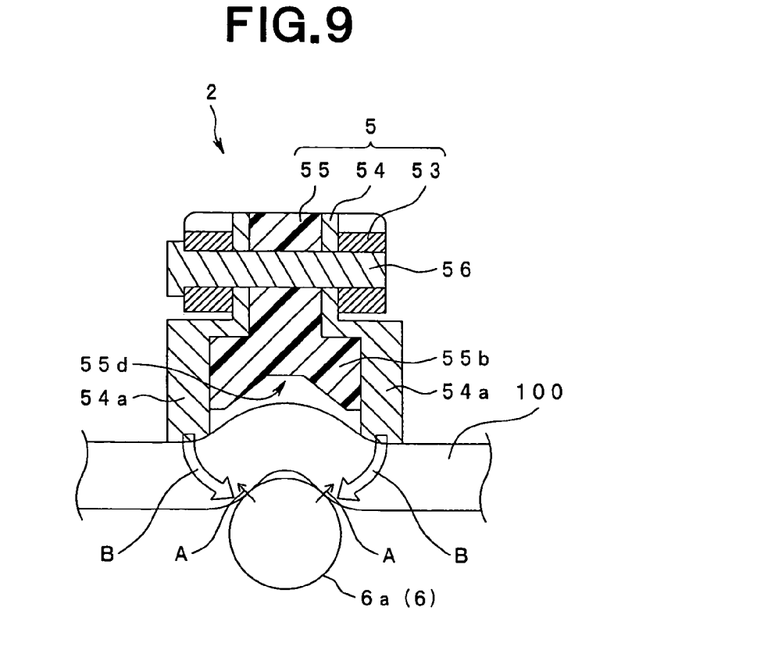
FIG. 9 is a diagram explaining coagulation in a first gripping state.

To perform coagulation and cutting of body tissue involving blood vessel clotting, the user inserts the sheath 21 of the ultrasonic instrument 2 into the abdominal cavity of a patient through, e.g., a trocar (not shown) penetrating through the abdominal wall. While viewing, e.g., endoscopic images displayed on a screen of a display device (not shown), the user allows the treatment tool 10 of the ultrasonic instrument 2 to face desired tissue. After that, the user controls the gripping member 5 and the probe 6 such that the desired tissue is located therebetween. Then, the user properly operates the control handle 27 provided for the control portion 20 to pivot the gripping member 5, thus gripping the tissue. As shown in FIG. 9, a blood vessel 100 in the tissue is gripped between the bifurcated toothed portion 54a of the diathermy member 54 and the outer surface of the distal end 6a of the probe 6. This state is termed a first gripping state in this specification. Further, the user turns on the switch 7b for coagulation and cutting in the foot switch 7 while viewing the gripping state on the screen.

Thus, a closed loop is formed between the diathermy surgical unit 4 and the tissue including the blood vessel 100 via the gripping member 5 and the probe 6 electrically connected to the ports 4d and 4e, so that the diathermy surgical unit 4 can apply high frequency current to the tissue including the blood vessel 100.

The high frequency current flows to the probe 6 through the blood vessel 100 from contact parts of the blood vessel 100 with the bifurcated toothed portion 54a constituting the diathermy member 54. In other words, paths for the flow of the high frequency current to the blood vessel 100 are generated as shown by arrows B in FIG. 9, whereby Joule heat is generated due to the impedance of the tissue including the blood vessel 100. The blood vessel 100 and surrounding tissue are coagulated, i.e., albuminoid degeneration is caused by the generated Joule heat. In addition, moisture contained in the tissue evaporates, so that the tissue becomes dry. In this step, the thickness of the blood vessel 100 and that of the surrounding tissue are gradually reduced.

Figure 10:
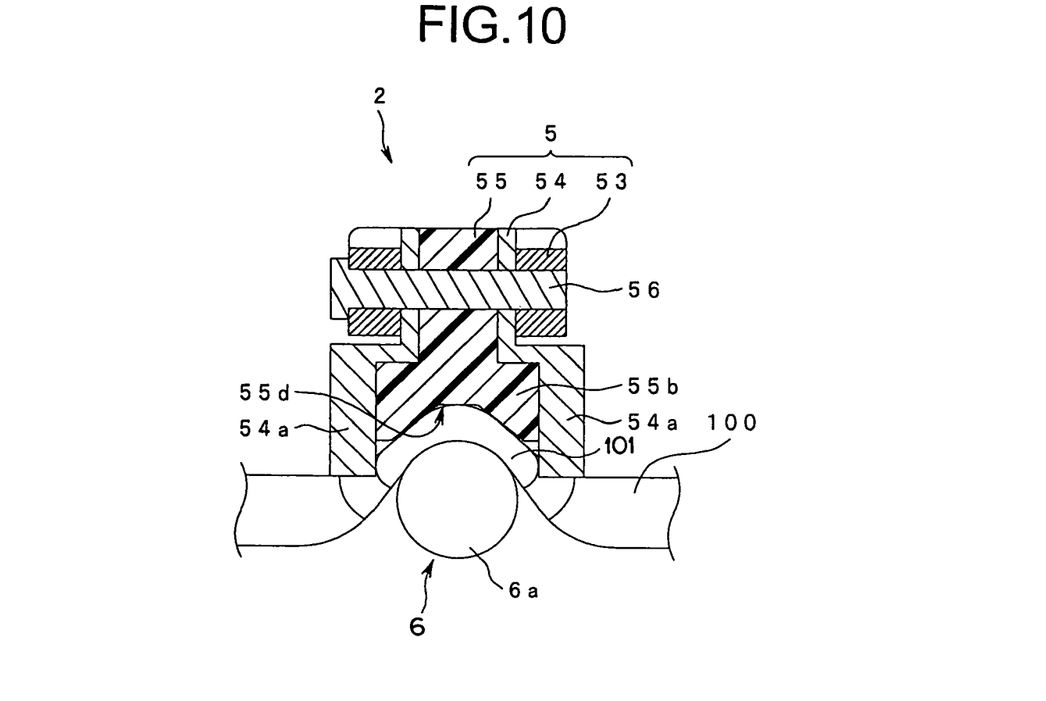
FIG. 10 is a diagram explaining cutting in a second gripping state.

In this instance, since the user holds the movable handle 27a, the gripping member 5 is pivoted so as to further approach the probe 6 as the thickness of the blood vessel 100 becomes thinner, thus accelerating coagulation and drying of the tissue. Consequently, the probe 6 is substantially fitted in the recess 55d of the ultrasonic treatment member 55 through the blood vessel 100, whose thickness is sufficiently reduced, as shown in FIG. 10. This state is termed a second gripping state in this specification. In other words, the positional relation between the gripping member 5 and the probe 6 reaches the second gripping state.

In this state, the blood vessel 100 coagulated by the high frequency current is pressed and held between the tissue pressing portion 55b of the ultrasonic treatment member 55 and the distal end 6a of the probe 6. In this instance, the ultrasonic surgical unit 3 outputs electric energy to drive the ultrasonic transducer. Thus, ultrasonic vibrations are transmitted from the distal end 6a to the blood vessel 100 pressed and held.

Figure 11:
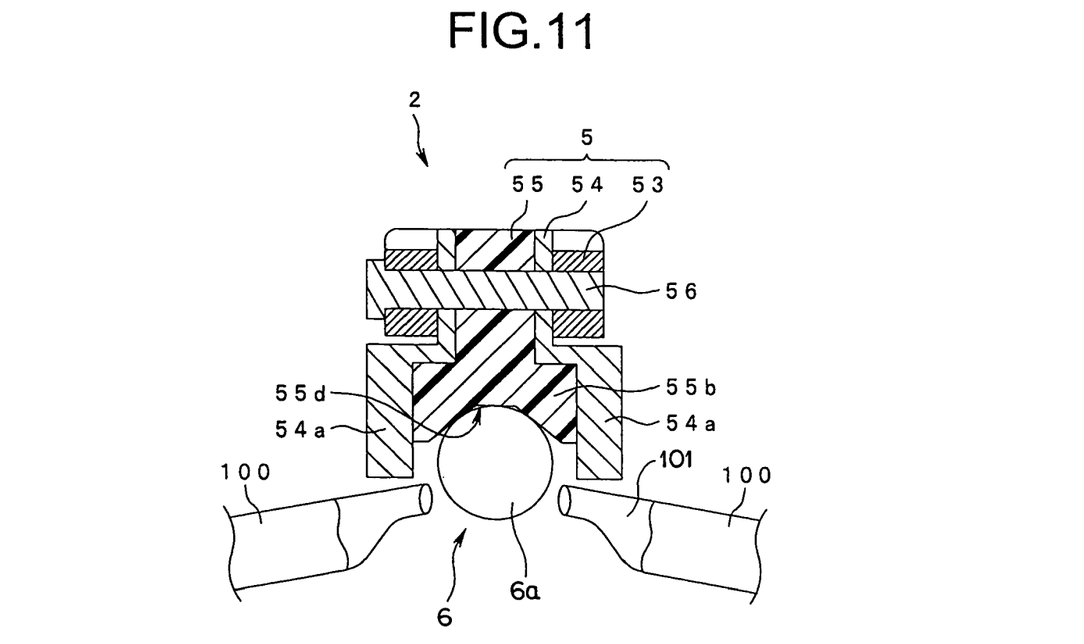
FIG. 11 is a diagram explaining a state in which a blood vessel including hemostatic part is cut.

Accordingly, the blood vessel 100 including coagulated part 101 is cut by frictional heat. When the ultrasonic treatment member 55 is come into contact with the distal end 6a of the probe 6 as shown in FIG. 11, the blood vessel 100 is cut. At that time, the blood vessel 100 in the vicinity of a cut position has been coagulated by the high frequency current, i.e., hemostasis has been performed. Therefore, treatment for the purpose of blood vessel clotting is completed.

As described above, in the ultrasonic instrument, the diathermy member is arranged at a predetermined position in the ultrasonic treatment member to assemble the gripping member for the ultrasonic instrument. In addition, in the ultrasonic instrument, a path for the flow of high frequency current is arranged such that the current output from the diathermy surgical unit to the first-electric-cable connecting portion during diathermy is fed back from the second-electric-cable connecting portion through body tissue to the diathermy surgical unit. Body tissue is held between the gripping member and the probe and, after that, the diathermy surgical unit supplies high frequency current to the tissue and the ultrasonic surgical unit simultaneously supplies electric energy to the ultrasonic transducer to generate ultrasonic vibrations. Accordingly, during a series of gripping operations, coagulation using high frequency current is performed in the first gripping state and cutting using ultrasonic vibrations is performed in the second gripping state. Thus, treatment for the purpose of blood vessel clotting can be completed by the series of gripping operations.

In addition, the diathermy member is provided at the predetermined position in the ultrasonic treatment member such that the toothed portion segments, also serving as the diathermy member, are arranged on both sides of the ultrasonic treatment member to be in contact with the probe. Accordingly, ultrasonic vibrations are transmitted from the probe to substantially intermediate tissue between tissue parts coagulated by high frequency current. Thus, the width of coagulation of the stump of a blood vessel can be substantially uniformed. Advantageously, treatment for the purpose of blood vessel clotting can be performed with higher reliability.

According to the present embodiment, after recognition of the first gripping state in which the blood vessel 100 is held between the distal end 6a of the probe 6 and the bifurcated toothed portion 54a of the diathermy member 54, the switch 7b for coagulation and cutting is turned on. Alternatively, the following procedure may be performed: After the first gripping state is recognized, the switch 7a for coagulation is turned on to perform only coagulation of tissue using high frequency current. The coagulated state is confirmed on the screen and, after that, the switch 7b is turned on to perform cutting of the tissue using ultrasonic vibrations in combination with high frequency current.

Figure 12:
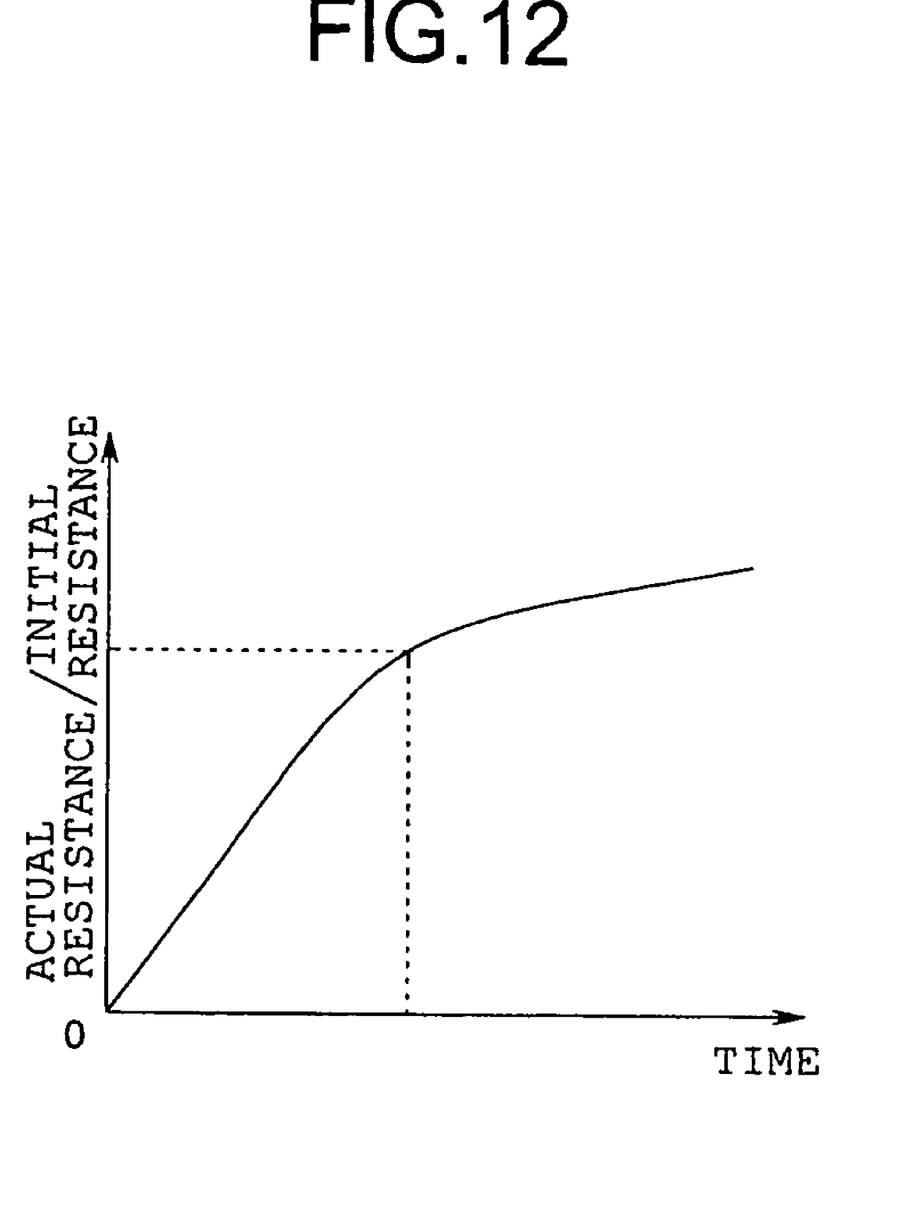
FIG. 12 is a graph showing a change in resistance of body tissue with time during coagulation using high frequency current flow.

As is generally known, supply of high frequency current for coagulation makes body tissue degenerate, so that the resistance of tissue, i.e., the impedance changes with time as shown in FIG. 12. Turning on the switch 7b for coagulation and cutting starts output of high frequency current from the diathermy surgical unit 4 and simultaneously starts measurement of the resistance of body tissue. When the resistance reaches a threshold value, shown by a broken line, indicating that the degree of coagulation has reached a certain level, output for ultrasonic vibration from the ultrasonic surgical unit 3 may be started.

Consequently, when the resistance of tissue processed by the diathermy surgical unit 4 reaches the threshold value, output can be automatically changed. The user can perform treatment while keeping a stable coagulated state of tissue without depending on viewing the screen.

In the present embodiment, the cross-section of the distal end 6a of the probe 6 is circular. The shape of the cross-section of the distal end 6a is not limited to a circle. The cross-section of the distal end 6a may be shaped as shown in FIGS. 13 to 16.

A modification of the probe and grip member will now be explained below with reference to FIGS. 13 to 16.

Figure 13:
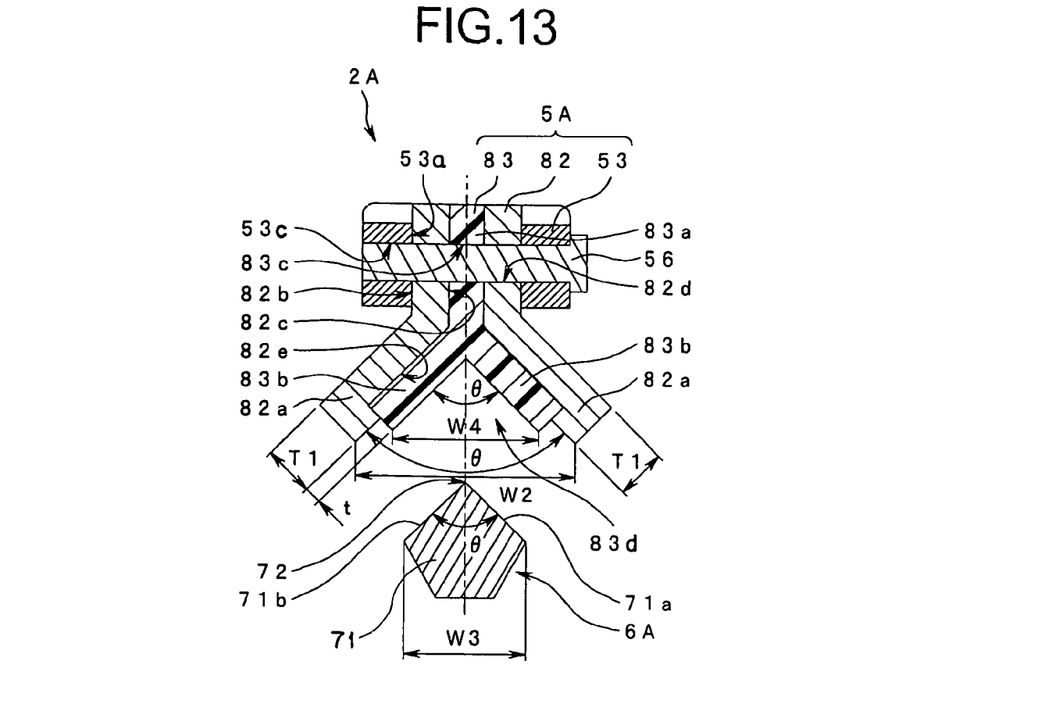
FIG. 13 is a cross-sectional view of a gripping member and a probe whose distal end has a pentagonal cross-section.

Referring to FIG. 13, according to the modification, a probe 6A constituting an ultrasonic instrument 2A is made of a conductive material. The shape of the cross-section of the distal end 71 of the probe 6A is, e.g., pentagonal. The shape of the cross-section thereof has line symmetry with respect to an axis of symmetry going through a vertex 72. A gripping member 5A, which is used in combination with the probe 6A, has also line symmetry with respect to a predetermined axis of symmetry. In the ultrasonic instrument 2A, the symmetry axis of the gripping member 5A is aligned with that going through the vertex 72 of the distal end 71.

An angle formed by two faces 71a and 71b sharing the vertex 72 of the distal end 71 is θ degrees. In the distal end 71, the vertex 72 is opposed to one face.

According to the modification, the gripping member 5A includes the main body 53, a diathermy member 82, and an ultrasonic treatment member 83. The main body 53 is made of a conductive material. The main body 53 has the screw hole 53c, into which the fixing screw 56 is screwed, at a predetermined position in each side adjacent to the first notch 53a.

The diathermy member 82 comprises a conductive material. The diathermy member 82 has a branch toothed gripping portion (hereinafter, referred to as a branch toothed portion) 82a, serving as a lower surface thereof in FIG. 13. An angle formed by segments of the branch toothed portion 82a is substantially identical to the angle θ of the vertex of the distal end 71 of the probe 6A.

An interval W2 between the segments of the branch toothed portion 82a is set in consideration of the width W3 of the distal end 71 of the probe 6A. Specifically, the interval W2 between the segments of the branch toothed portion 82a is larger than the width W3 of the distal end 71 by a predetermined amount. The thickness T of each segment of the branch toothed portion 82a is appropriately set in consideration of the rigidity and a target range to be coagulated.

On the lower surface of the branch toothed portion 82a opposed to the faces 71a and 71b, serving as the outer surfaces of the distal end 71, teeth for securely gripping body tissue may be arranged in, e.g., rows.

The diathermy member 82 has notches (not shown) extending in the lengthwise direction thereof in both side surfaces to adjust the width of the upper part of the diathermy member 82. Forming the notches in the diathermy member 82 provides a projection 82b in the upper part of the diathermy member 82. The projection 82b is arranged in the first notch 53a. The diathermy member 82 has a through-hole 82c in which the ultrasonic treatment member 83 is arranged at a predetermined position. The through-hole 82c is, e.g., rectangular. In addition, the diathermy member 82 has holes 82d, through which the fixing screw 56 is inserted. Each hole 82d is formed at a predetermined position in the corresponding side of the projection 82b such that the holes 82d face each other with the through-hole 82 therebetween.

The ultrasonic treatment member 83 is made of at least a flexible non-damping material. The cross-section of the ultrasonic treatment member 83 is inverted Y-shaped. The ultrasonic treatment member 83 includes a projection 83a for attachment and a tissue pressing portion 83b. The ultrasonic treatment member 83 may be made of a conductive material obtained by mixing conductive particles into the flexible non-damping material.

The projection 83a is shaped so as to be received in the through-hole 82c of the diathermy member 82. The projection 83a of the ultrasonic treatment member 83 has a hole 83c, in which the fixing screw 56 is fitted, in a predetermined position. The hole 83c is provided on the side face of the projection 83a.

The tissue pressing portion 83b has a recess 83d which is inverted V-shaped. The angle of the inverted V-shaped recess is substantially identical to the vertex angle θ of the distal end 71. The width W4 of the recess 83d in the tissue pressing portion 83b is smaller than the interval W2 between the segments of the branch toothed portion 82a. The inverted V-shaped recess of the tissue pressing portion 83b is designed so that the recess is in tight contact with the faces 71a and 71b of the distal end 71 of the probe 6A.

According to the modification, a recess 82e for receiving the tissue pressing portion is formed in the branch toothed portion 82a of the diathermy member 82 such that each step t has a predetermined height. In other words, each step t is defined by one face of the branch toothed portion 82a and one face of the tissue pressing portion 83b. The structure of the ultrasonic instrument 2A is the same as that of the above-described ultrasonic instrument 2.

The operation of the ultrasonic coagulation and cutting apparatus having the ultrasonic instrument 2A with the above-described structure will now be described.

Figure 14:
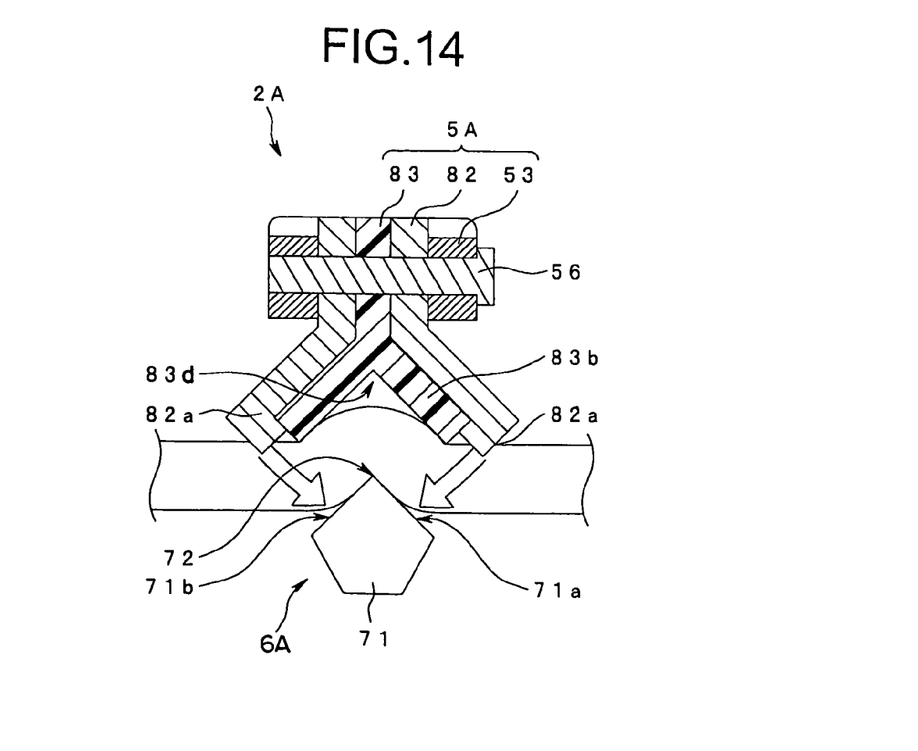
FIG. 14 is a diagram explaining coagulation in the first gripping state.

For example, to perform coagulation and cutting of body tissue including a blood vessel, a user inserts the sheath 21 connected to the ultrasonic instrument 2A into the abdominal cavity of a patient. The user controls the gripping member 5A and the probe 6A such that desired tissue is located therebetween. Then, the user properly operates the control handle 27 provided for the control portion 20 to pivot the gripping member 5A, thus gripping the tissue. As shown in FIG. 14, a blood vessel 100 in the tissue is gripped between the branch toothed portion 82a of the diathermy member 82 and the faces 71a and 71b of the distal end 71 of the probe 6A, i.e., the first gripping state is provided. Further, the user operates the movable handle 27a to move the gripping member 5A toward the probe 6A and also turns on the switch 7b for coagulation and cutting in the foot switch 7.

Thus, a closed loop is formed between the diathermy surgical unit 4 and the tissue including the blood vessel 100 via the gripping member 5A and the probe 6A electrically connected to the ports 4d and 4e, so that bipolar current is applied to the tissue including the blood vessel 100.

High frequency current flows through the blood vessel 100 as shown by arrows in FIG. 14, thus starting coagulation. More specifically, the high frequency current flows to the probe 6A through the blood vessel 100 from contact parts of the blood vessel 100 with the branch toothed portion 82a constituting the diathermy member 82. After the coagulation using high frequency current is started, moisture contained in the blood vessel 100 and surrounding tissue evaporates, thus accelerating drying of the tissue. This leads to a reduction in volume of the tissue. In other words, the thickness of the blood vessel 100 is gradually reduced.

In this instance, since the user holds the movable handle 27a, the gripping member 5A is pivoted so as to further approach the probe 6A as the thickness of the blood vessel 100 becomes thinner.

Figure 15:
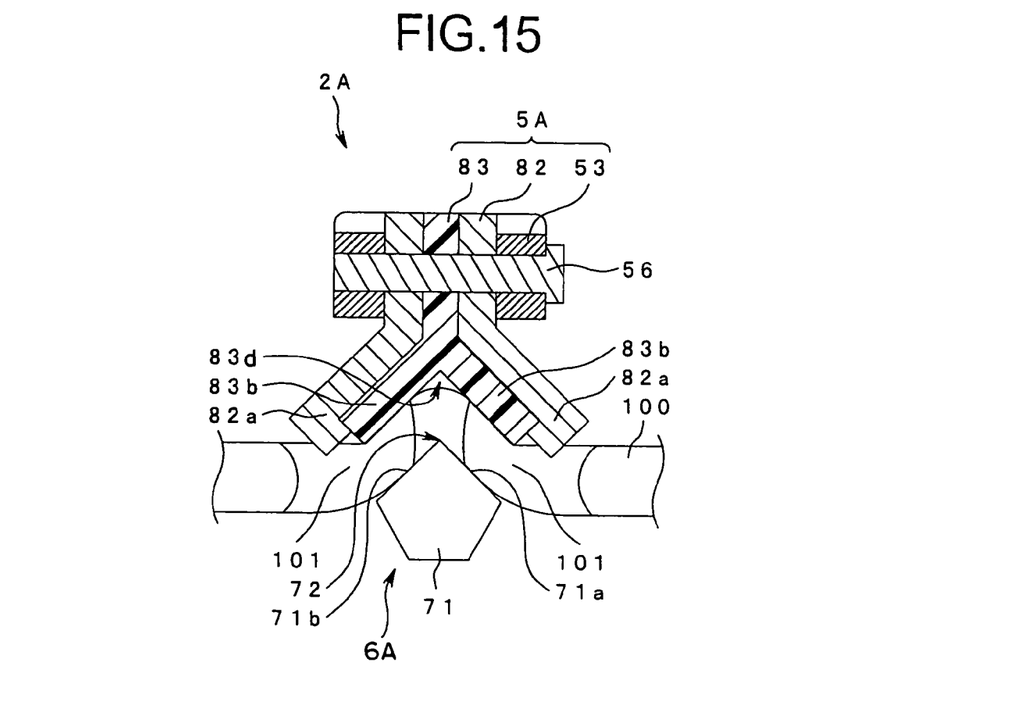
FIG. 15 is a diagram explaining cutting in the second gripping state.

Accordingly, coagulation and drying of the tissue are accelerated. Consequently, the probe 6A is substantially fitted to the recess 83d of the ultrasonic treatment member 83 through the blood vessel 100 whose thickness is sufficiently reduced as shown in FIG. 15. In other words, the positional relation between the gripping member 5A and the probe 6A reaches the second gripping state.

Figure 16:
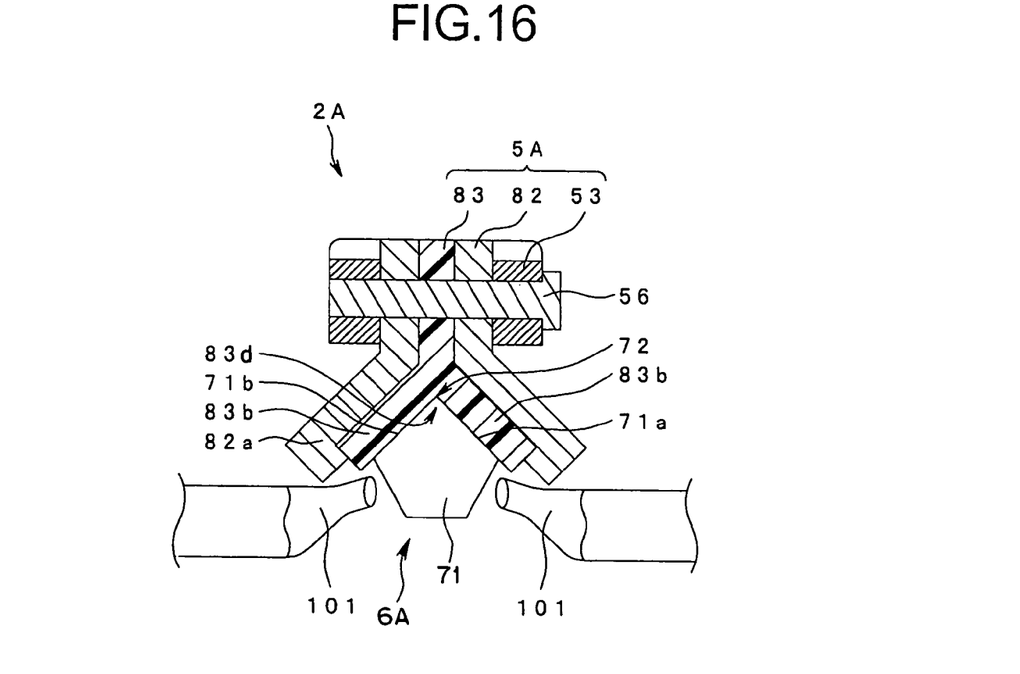
FIG. 16 is a diagram explaining a state in which a blood vessel including hemostatic part is cut.

In this state, the blood vessel 100 including part 101 coagulated by the high frequency current is pressed and held between the tissue pressing portion 83b of the ultrasonic treatment member 83 and the faces 71a and 71b of the distal end 71 of the probe 6A. In this instance, the ultrasonic surgical unit 3 supplies electric energy to the ultrasonic transducer to generate ultrasonic vibrations. Thus, the ultrasonic transducer transmits ultrasonic vibrations to the pressed and held blood vessel 100 through the distal end 71 of the probe 6A. Consequently, frictional heat is transmitted to the whole of a contact area of the held and pressed blood vessel 100, thus accelerating coagulation of the blood vessel 100. After that, when degeneration of the blood vessel 100 by the frictional heat is further advanced and the thickness of the blood vessel 100 is sufficiently reduced, flat portions of the tissue pressing portion 83b are brought into tight contact with the faces 71a and 71b of the distal end 71 and the vertex 72 is come into contact with the recess 83d of the tissue pressing portion 83b of the ultrasonic treatment member 83, so that the blood vessel 100 located in the vicinity of the vertex 72 is cut as shown in FIG. 16.

In the above-described process, the blood vessel 100 in the vicinity of the cut position is coagulated by the high frequency current, i.e., hemostasis is performed. In addition, the blood vessel 100 is coagulated using ultrasonic vibrations and is then cut. Therefore, treatment for the purpose of blood vessel clotting is completed.

As described above, since the cross-section of the distal end of the probe is pentagonal, in the first gripping state, the faces sharing one vertex of the distal end is in contact with body tissue to secure an enough contact area. In this state, high frequency current is immediately applied to the body tissue, whereby coagulation can be reliably performed. In addition, in the second gripping state, while the sharp vertex is in contact with the body tissue, the body tissue can be rapidly cut using ultrasonic vibrations. Thus, the coagulation and cutting capabilities can be improved.

In addition, since the recess is provided and each step is set to the predetermined height, the body tissue can be securely pressed such that the body tissue is thinned to a desired thickness during coagulation using high frequency current.

The shape of the cross-section of the distal end constituting the ultrasonic probe is not limited to the above-described pentagon or circle. A shape having line symmetry, such as a triangle or a tear-drop shape, may be used.

For the purpose of reducing cutting time, the distal end of the probe may be shaped so as to enhance an ultrasonic cutting effect. Specifically, the diameter or width of the distal end may be reduced. On the other hand, when a higher coagulation effect is needed, the waveform of high frequency current applied and applying time may be changed to enhance the coagulation effect of high frequency current.

Having described the preferred embodiment and modification of the invention referring to the accompanying drawings, it should be understood that the present invention is not limited to the precise embodiment and modification and various changes and modifications thereof could be made by one skilled in the art without departing from the spirit and scope of the invention as defined in the appended claims.

What is claimed is:

1. An ultrasonic coagulation and cutting apparatus comprising:
an ultrasonic transducer for converting electric signals into ultrasonic vibrations to perform a treatment using ultrasonic vibrations on body tissue;
a conductive probe which has a proximal end and a distal end, the proximal end being connected to the ultrasonic transducer in order to transmit ultrasonic vibrations generated by the ultrasonic transducer to the distal end, and which is electrically connected to a high frequency power supply for generating high frequency current; and
a gripping member configured to be movable closer to and farther away from the distal end of the probe, and capable of gripping the body tissue between it and the distal end of the probe,
wherein the gripping member includes:
a first contact portion configured by a conductive member, the first contact portion being electrically connected to the high frequency power supply that generates the high frequency current, for contacting the body tissue for performing treatment with the high frequency current, and
a second contact portion configured by an insulating material, for contacting the body tissue for performing treatment with the ultrasonic vibrations, and
wherein the second contact portion is provided at a position of the gripping member opposed to the probe, and the first contact portion is provided on both sides of the second contact portion and projected further toward the probe than the second contact portion.

2. The apparatus according to claim 1, wherein the gripping member includes
   a conductive segment and
   an insulating segment, the insulating segment serving as a probe contact member for preventing the conductive segment from being in direct contact with the probe when the gripping member is moved closer to the probe.

3. The apparatus according to claim 1, wherein the first contact portion of the gripping member includes a toothed gripping portion for pressing the body tissue between the gripping member and the distal end of the conductive probe.

4. The apparatus according to claim 1, wherein
   a path for the flow of high frequency current for coagulation from the gripping member to the probe is provided in a first gripping state in which the body tissue is gripped between the first contact portion of the gripping member and the probe, and
   ultrasonic vibrations transmitted from the ultrasonic transducer to the probe are transferred to the body tissue in addition to the flow of high frequency current from the gripping member to the probe in a second gripping state in which the body tissue is gripped between the first and second contact portions of the gripping member and the probe.

5. The ultrasonic coagulation and cutting apparatus according to claim 1, wherein the second contact portion has a width larger than an outer diameter of the probe.

6. The ultrasonic coagulation and cutting apparatus according to claim 1, further comprising a detecting portion for detecting an impedance of the body tissue when the high frequency current is supplied from the high frequency power supply to perform treatment.

7. The ultrasonic coagulation and cutting apparatus according to claim 6, further comprising an output control portion for changing from the treatment using the high frequency current to the treatment using the ultrasonic vibrations when the detecting portion has detected that the impedance of the body tissue has reached a threshold as a result of the treatment.

\* \* \* \* \*